United States Patent
Shanks (10) Patent No.: US 9,541,436 B2
(45) Date of Patent: Jan. 10, 2017

(54) DISTRIBUTED TWO DIMENSIONAL FLUID SENSOR

(71) Applicant: Zenith Oilfield Technology Ltd., Inverurie (GB)

(72) Inventor: David Sirda Shanks, Aberdeen (GB)

(73) Assignee: Lufkin Industries, LLC, Lufkin, TX (US)

( * ) Notice: Subject to any disclaimer, the term of this patent is extended or adjusted under 35 U.S.C. 154(b) by 412 days.

(21) Appl. No.: 14/358,189

(22) PCT Filed: Nov. 21, 2012

(86) PCT No.: PCT/GB2012/052877
§ 371 (c)(1),
(2) Date: May 14, 2014

(87) PCT Pub. No.: WO2013/076479
PCT Pub. Date: May 30, 2013

(65) Prior Publication Data
US 2014/0290335 A1 Oct. 2, 2014

(30) Foreign Application Priority Data

Nov. 22, 2011 (GB) .................................. 1120149.8

(51) Int. Cl.
*G01F 1/74* (2006.01)
*E21B 47/10* (2012.01)
(Continued)

(52) U.S. Cl.
CPC ............. *G01F 1/74* (2013.01); *E21B 43/2401* (2013.01); *E21B 47/1005* (2013.01);
(Continued)

(58) Field of Classification Search
CPC .................................. G01F 1/74; G01N 25/18
See application file for complete search history.

(56) References Cited

U.S. PATENT DOCUMENTS 3,981,187 A 9/1976 Howell
4,267,727 A 5/1981 Hoppe
(Continued)

FOREIGN PATENT DOCUMENTS

CA 2323234 4/2001
CN 1367858 9/2002
(Continued)

OTHER PUBLICATIONS

Unofficial English translation of Office Action issued in connection with corresponding CN Application No. 201280056890.7 on Dec. 2, 2015.
(Continued)

*Primary Examiner* — Paul West
*Assistant Examiner* — Mark A Shabman
(74) *Attorney, Agent, or Firm* — Crowe & Dunlevy, P.C.

(57) ABSTRACT

A fluid measurement system and method for determining distributed measurement of a fluid type and a fluid velocity in a wellbore, pipeline or other conduit in which fluid is moving. Measurement is made by immersing one or more cables having sequential sampling sections in the fluid and monitoring a cooling effect across a cable on the sampling sections and the response to injection of a high frequency pulse each sampling section. A probabilistic model is then used to determine the distributed velocity and fluid types along the conduit.

20 Claims, 10 Drawing Sheets

(51) Int. Cl.
| | |
|---|---|
| *E21B 47/12* | (2012.01) |
| *G01F 25/00* | (2006.01) |
| *G01F 1/688* | (2006.01) |
| *G01F 23/284* | (2006.01) |
| *G01N 27/22* | (2006.01) |
| *E21B 43/24* | (2006.01) |
| *G01N 25/18* | (2006.01) |
| *G01N 27/02* | (2006.01) |
| *G01D 5/353* | (2006.01) |

(52) U.S. Cl.
CPC .......... *E21B 47/123* (2013.01); *G01F 1/6884* (2013.01); *G01F 23/284* (2013.01); *G01F 25/0007* (2013.01); *G01N 25/18* (2013.01); *G01N 27/02* (2013.01); *G01N 27/221* (2013.01); *G01D 5/35364* (2013.01); *G01D 5/35367* (2013.01)

(56) References Cited

U.S. PATENT DOCUMENTS

| | | | |
|---|---|---|---|
| 4,429,273 A | 1/1984 | Mazzagatti | |
| 4,570,492 A * | 2/1986 | Walsh | G01F 1/708 204/411 |
| 4,597,183 A | 7/1986 | Broding | |
| 4,909,855 A | 3/1990 | Burley | |
| 5,010,316 A | 4/1991 | Burley | |
| 5,025,222 A | 6/1991 | Scott et al. | |
| 5,030,294 A | 7/1991 | Burley | |
| 5,033,297 A | 7/1991 | Gustafson | |
| 5,132,903 A | 7/1992 | Sinclair | |
| 5,231,880 A | 8/1993 | Ward et al. | |
| 5,571,394 A | 11/1996 | Hettiarachchi et al. | |
| 5,600,073 A * | 2/1997 | Hill | G01B 5/28 73/30.03 |
| 5,818,241 A * | 10/1998 | Kelly | G01N 33/24 324/640 |
| 5,926,024 A * | 7/1999 | Blount | G01N 22/00 324/324 |
| 6,064,002 A | 5/2000 | Hayami et al. | |
| 6,227,045 B1 | 5/2001 | Morse et al. | |
| 6,441,622 B1 * | 8/2002 | Wrzesinski | G01N 22/04 324/533 |
| 6,539,795 B1 | 4/2003 | Scherpenisse et al. | |
| 7,017,417 B2 | 3/2006 | Daigle | |
| 7,190,280 B2 | 3/2007 | Hall et al. | |
| 7,409,858 B2 | 8/2008 | Dria et al. | |
| 7,730,774 B2 | 6/2010 | Glasbergen et al. | |
| 8,074,713 B2 | 12/2011 | Ramos et al. | |
| 8,973,434 B2 | 3/2015 | Albrecht et al. | |
| 2003/0051558 A1 * | 3/2003 | Melnikov | G01F 1/663 73/861.27 |
| 2003/0122535 A1 * | 7/2003 | Williams | E21B 43/2401 324/107 |
| 2004/0031681 A1 | 2/2004 | Jett et al. | |
| 2004/0059513 A1 | 3/2004 | Bittar et al. | |
| 2004/0096614 A1 | 5/2004 | Quigley et al. | |
| 2005/0034873 A1 | 2/2005 | Coon et al. | |
| 2005/0083062 A1 * | 4/2005 | Couch | G01F 23/284 324/337 |
| 2005/0172721 A1 | 8/2005 | Daigle | |
| 2005/0265121 A1 | 12/2005 | Scott | |
| 2005/0274513 A1 * | 12/2005 | Schultz | E21B 43/04 166/254.2 |
| 2006/0108112 A1 | 5/2006 | Simon | |
| 2006/0214098 A1 | 9/2006 | Ramos | |
| 2007/0071612 A1 | 3/2007 | Yuratich | |
| 2007/0119244 A1 | 5/2007 | Goodwin et al. | |
| 2007/0125163 A1 | 6/2007 | Dria et al. | |
| 2007/0158064 A1 | 7/2007 | Pribnow et al. | |
| 2007/0239360 A1 | 10/2007 | Rabinovich et al. | |
| 2008/0048669 A1 | 2/2008 | Scherber et al. | |
| 2008/0061789 A1 | 3/2008 | Coates | |
| 2008/0083273 A1 | 4/2008 | Sroka et al. | |
| 2008/0185138 A1 | 8/2008 | Hernandez-Solis et al. | |
| 2008/0224705 A1 | 9/2008 | Simon et al. | |
| 2008/0317095 A1 | 12/2008 | Hadley et al. | |
| 2009/0277629 A1 | 11/2009 | Mendez et al. | |
| 2009/0326826 A1 | 12/2009 | Hull et al. | |
| 2010/0223011 A1 | 9/2010 | Parsche | |
| 2010/0254650 A1 | 10/2010 | Rambow | |
| 2011/0007776 A1 | 1/2011 | Yamamoto | |
| 2011/0081256 A1 | 4/2011 | Thompson et al. | |
| 2011/0188344 A1 | 8/2011 | Hartog et al. | |
| 2011/0311179 A1 | 12/2011 | Greenaway | |
| 2012/0075951 A1 | 3/2012 | Johnson et al. | |
| 2013/0091942 A1 | 4/2013 | Samson et al. | |
| 2014/0069810 A1 | 3/2014 | Tachibana et al. | |
| 2015/0090040 A1 | 4/2015 | Schumacher et al. | |
| 2015/0233211 A1 | 8/2015 | Bujold et al. | |

FOREIGN PATENT DOCUMENTS

| | | |
|---|---|---|
| CN | 1723332 | 1/2006 |
| CN | 1723332 A | 1/2006 |
| CN | 2900784 | 5/2007 |
| CN | 101313127 | 11/2008 |
| CN | 101598581 | 12/2009 |
| CN | 201396147 | 2/2010 |
| DE | 2521411 | 11/1976 |
| DE | 19950111 | 2/2001 |
| DE | 10052922 | 5/2002 |
| EP | 0508894 | 10/1992 |
| EP | 1098197 A2 | 5/2001 |
| EP | 1574853 A1 | 9/2005 |
| GB | 2159663 | 12/1985 |
| GB | 2246866 | 2/1992 |
| GB | 2467177 | 7/2010 |
| GB | 2484990 | 5/2012 |
| GB | 2495132 | 4/2013 |
| GB | 2495132 A | 4/2013 |
| WO | 9100996 A1 | 1/1991 |
| WO | 0011317 | 3/2000 |
| WO | 0011317 A1 | 3/2000 |
| WO | 2007109772 A2 | 9/2007 |
| WO | 2011044023 | 4/2011 |
| WO | 2011044023 A2 | 4/2011 |
| WO | 2012/052764 | 4/2012 |

OTHER PUBLICATIONS

Kane, et al., "Applications of time domain reflectometry to landslide and slope monitoring", TDR 2002—Second International Symposium and Workshop on Time Domain Reflectometry for Innovative Geotechnical Application, pp. 1-14, Dec. 31, 2001.

Jie, et al., "Introduction to Numerical Simulation of Electrical Logging and Its Development Trend", Well Logging Technology, vol. No. 34, Issue No. 1, pp. 1-5, Feb. 28, 2010.

Feldhoff, R. International Search Report for International Patent Application PCT/GB2012/052877, dated Feb. 19, 2013, European Patent Office.

Feldhoff, R. Written Opinion for International Patent Application PCT/GB2012/052877, dated Feb. 19, 2013, European Patent Office.

* cited by examiner

DISTRIBUTED TWO DIMENSIONAL FLUID SENSOR

The present invention relates to fluid measuring techniques in the oil and gas industry and in particular, though not exclusively, to a fluid measurement system and method for determining mixed fluid compositions and their flow rates in moving fluid mixtures present in conduits such as well bores and pipelines.

The oil and gas industry is very dependent on well bore measuring techniques to provide information about what is actually happening deep in a well bore. Many surveys are done before oil or gas is produced, including seismic and rock porosity, water content and micro seismic. However, there are few methods of obtaining data which gives a broad measurement of the behaviour of the well over its whole length, especially while the well is being produced.

Point pressure and temperature sensors have been in commonplace use since the 1940's and production logging tools are also now customarily used. It is quite common in the oil and gas industry to run logging tools which measure water cut and well bore resistivity, and also optical distributed temperature sensing systems into oil wells to measure the temperature profile over the complete length of the well bore.

Point sensors only provide indications of what is happening at the position of the sensor. Logging tools measure the complete well bore, but using single sensors which traverse the well bore while recording. This does not log the whole well bore in real time and they can only be run periodically. Logging tools are also difficult to run, when there are pumps in the well bore. Distributed temperature measurement is limited by the fact that, while the temperature profile can be interpreted to give information about other behaviour in the well bore, the temperature information in its raw state is not immediately useful in terms of determining the fluid produced (or injected), or more importantly the fluid flow rates.

The oil and gas industry is under pressure to achieve greater efficiency and increase production rates, all of which requires more understanding of reservoir storage and production behaviour. This has created a need for more 2 dimensional and 3 dimensional measurements of reservoir behaviour.

Prior art systems exist which utilise the cooling effect of moving fluid on a heated cable for flow measurement in a well bore. WO00/11317 (EP 1109990 and US2003/0122535) to Baker Hughes Inc. provides a heater cable that may be deployed in a wellbore to elevate the temperature of the wellbore above the temperature of the surrounding fluid and the formation. One or more fiber optic strings are included in or are carried by the heater cable. The heater cable carrying the fiber optics is placed along the desired length of the wellbore. At least one fiber optic string measures temperature of the heater cable at a plurality of spaced apart locations. Another string may be utilized to determine the temperature of the wellbore. In one aspect of this invention, the heater cable is heated above the temperature of the wellbore. The fluid flowing from the formation to the wellbore lowers the temperature of the cable at the inflow locations. The fiber optic string provides measurements of the temperature along the heater cable. The fluid flow is determined from the temperature profile of the heater cable provided by the fiber optic sensors.

The major problem and drawback of this basic technique is that oil field producing wells generally contain more than one fluid, and are more generally multi-phase containing water, oil and gas. The thermal conductivity of oil water and gas are different, and so the cooling effect created on the heated sensor cable will depend not only on the flow rate but also the particular fluid mixture at the heated cable and each fibre optic sensor is located within at the time of the measurement. As the prior art cannot distinguish between these different fluid types, the device can only provide a calculation of average flow rate with an assumption that only a single fluid type is present, or an estimation of the fluid mixture present at any point.

A further disadvantage in this technique is the requirement that the temperature of the wellbore must be elevated to be above that of the surrounding fluid and the formation. This requires large amounts of power to be applied to the heater cable which is impractical for long sampling lengths and in high flow rates, especially in water flows, is typically not achievable.

A system which can detect different fluid types has been proposed by Chevron USA Inc. in WO2011/044023. This discloses a system which includes a pulse generator to generate a pulse of electromagnetic energy to propagate along a wellbore towards a surface of a fluid, a detector to detect a portion of the electromagnetic pulse reflected from the surface of the fluid and propagate along the wellbore towards the detector, and a processor to analyse detected signals to determine a level of the surface of the fluid. This technique uses the principle of transmission lines which are known for measuring interfaces between fluids by determining that a change in the dielectric properties between the transmission lines has occurred.

A major drawback of WO2011/044023 is that it can only determine fluid levels in static, non-flowing, well bores. It has further disadvantages in the number of unwanted reflections which are present giving false readings. These reflections occur at any dielectric interface through the well bore and as the transmission line is preferably created from the casing together with tubing located within the casing, acting as a central conductor, all connection points such as the casing joints will provide unwanted reflections.

To overcome this disadvantage the system proposes markers to give reflections at known depths to assist in determining the true reflection from the fluid surface. These may take the form of a coaxial choke or wiper arm which provide a local reduction in the dielectric properties over the length of the marker. Unfortunately, such markers do not work. This is because a reflection will occur when the pulse reaches the marker and when the pulse exits the marker due to the change in dielectric properties created by the marker. Each reflection will provide a response being the precise inverse of the other and, over the short length of marker, the responses will cancel each other out.

To also overcome the problems of unwanted reflections, the system provides an embodiment using a spooled pair of conductors as may be run into the well bore as part of a dewatering system. A disadvantage of this system is in the long cable lengths used to access deep wells where the pump is located. As the pulse generator is located at the surface, the pulse will have dispersed and reduced in signal strength by the time it has traveled to the fluid surface level it is supposed to measure. The same effects will occur on the reflected signal, which will, by its very nature of being a reflected response, be of reduced signal strength. If the system includes markers or a second fluid level is required to be determined, in practise, the return responses are indistinct at the surface of the well bore.

A combination of WO 00/11317 and WO 2011/044023 cannot provide a system to measure fluid flow rates and determine fluid composition in a mixed fluid moving through a well bore. Inputting a single pulse into a flowing mixture of fluids will generate multiple reflections at all the fluid interfaces of the mixture due to the turbulent nature and thus, the returned signals will be 'chaos'. If the fluid is well mixed i.e. an emulsion, as would occur in an energetic well, there will be no reflections as there are no interfaces between the fluids and again, a calculation cannot be made.

It is therefore an object of the present invention to provide a system and method of measuring flow rates across fluid mixtures to provide a distributed fluid velocity measurement in two dimensions (typically depth and time).

According to a first aspect of the invention there is provided a fluid measurement system for measuring moving fluid along a length of a conduit comprising:

an elongate structure physically divided into a plurality of sampling sections along it's length and located in the conduit;

a heated core element and a distributed temperature sensor along the length of the structure, said heated core element and said distributed temperature sensor arranged so that the temperature sensor is physically between the heated core and an outside surface of the structure to sense heat loss from the core to its environment, and said heated core element and said distributed temperature sensor are encased in a material which thermally isolates the heated core element from the moving fluid.

one or more wires arranged along the length of the structure, said wires being configured to be usable as a transmission line;

at least one high frequency pulse generator for injecting a high frequency pulse along at least one sampling section of the structure; and a data acquisition unit for recording the heat loss along the distributed temperature sensor and the velocity of the high frequency pulse along each sampling section of the structure to provide a two-dimensional measure of fluid type and velocity simultaneously for the length of the conduit.

It has been found and presented in Applicant's co-pending patent application GB1116855.6, that the velocity of propagation of a pulse along a wire varies depending on the type of fluid in which the wire is immersed as the characteristic impedance of the wire varies depending on the fluid surrounding the wire. The precise mechanism being that the signal velocity, group and phase vary depending on the dielectric and conductive properties of the fluids. The velocity in gas is the fastest, oil slower and water slower still. Therefore the time taken for a signal to reach the bottom of the wire and be recorded at surface is a measure of the composition of the fluids it has passed through. So if a wire was installed in a moving mixture of oil and gas or oil and water the average velocity of propagation is a measure of the mixture of the fluids over the length of that wire. Thus with the flow rate determined from the distributed temperature sensor and the fluid composition determined from the pulse response in the wire over multiple short sampling sections, a two-dimensional measure of fluid type and flow rate can be derived for the length of the well bore.

Preferably, the structure includes periodic electronic measurement modules at each sampling section to split the structure into measurement zones. Alternatively, measurement zones can be created by alternating geometry in the transmission line segments between each sampling section. In this way, the structure of the cable and the sensor cable can be split into measurement zones producing a two-dimensional measure of fluid type and velocity simultaneously.

In addition combining the thermal heat loss measurement adds a further important measurement which allows determination of gas content. The thermal conductivity of gas is considerably less than that of both oil and water, and as such a pure gas flow will have a calibrated heat loss vs. velocity behaviour which does not overlap any of the fluid velocity calibrations. So there is a range of medium to high gas volume fractions which can be detected from the heated cable system purely because of the high temperatures measured while the heaters are switched on. While at low gas volume fractions this will not provide unique results, this provides a region of operation for the system which will provide good results in three phase flows, since the thermal output will, when combined with the fluid properties measured from the pulse velocity, will allow determination of the volume fraction and velocity of all three phases.

Further the structure provides thermal isolation of the heater from the well bore fluids, which allows use of a relatively low powered heater system. The temperature sensing system is also arranged to be physically between the heater and the fluid within the structure. So rather than using the heater to heat the fluid the heater is used to raise the core of the sensor cable structure and the cooling effect on the outer surface is used to measure flow rather than the direct cooling of the heating element as described in hot wire anemometry. This then provides a low powered system capable of measuring high flow rates in high thermal conductive fluids such as water.

Preferably the elongate structure is a cable. In this way, the system can be easily deployed into a wellbore, but could be used in a pipeline or storage tank.

The distributed temperature sensor may comprise a fibre-optic distributed temperature sensor. The heated core element may comprise a resistance wire. The distributed temperature sensor may be coiled helically around the heated core element. The elongate structure may include an insulation layer enclosing the heated core element. Preferably the distributed temperature sensor is embedded within the insulation layer. Alternatively there may be a second layer around the insulation layer and the distributed temperature sensor may be embedded in the second layer.

The system may further comprise control means for controlling the heating of the heated core element. Preferably the control means is located with the data acquisition unit so that data on the heating can be processed in the unit.

Preferably the high frequency signal generator provides a pulse being a signal with a fast rise time, typically <5 nS. The signal may be selected from a group comprising: modulated carriers, pulse streams, pulse sequences and shorter simpler pulse bursts.

Preferably the wire has a plurality of propagation sections, one for each sampling section, with neighbouring propagation sections having different characteristic impedances. In this way, measurements can be made over each propagation section giving an array of fluid mixture measures and producing a 2-dimensional image of fluid properties. More preferably the wire is arranged helically along the structure. In this way, the effective spatial resolution of the system is increased.

Preferably, the data acquisition unit compares the measured heat loss and the velocity of the high frequency signal response to a probabilistic mathematical model of the well bore to determine the mixture of fluids in each propagation section. Advantageously, the data acquisition unit may interpret the response for a section by using the average properties in the adjacent sections of the well bore. Additionally, the data acquisition unit may provide interpretation by looking at incremental changes between sections. In this way, while a two phase fluid mixture such as oil and gas or water and gas or water and oil, is easily determined, interpretation and use of a model will aid determination where there are three phases of fluids present, water oil and gas simultaneously. Thus the potentially chaotic return signals can be analysed as they are over shorter lengths and the probabilistic modelling is ideal for chaotic complex regimes.

Preferably, measurement electronics are mounted at either end of the elongate structure. The measurement electronics may also be mounted at each end of each sampling section. Preferably the measurement electronics comprises the data acquisition unit. The measurement electronics may also comprise a signal generator. By taking measurements at both ends of the member or section, the system may be effective in deep well bores to operate over long propagation sections by limiting the effects from losses in the cable and also from progressively more confusing responses from the further away sections of the cable.

Preferably also, PN sequence signal sources are used which can be run both in real time and continuously in parallel. Advantageously, orthogonal PN sequences may be used so that two or more pulse sequences do not interfere with one another.

Preferably the system includes an analogue detection unit. Preferably also the system includes means to analyse the analogue reflection response. In this way, while the average fluid mixture is measured, information about where the fluid mixture changes over a section can be obtained. The primary measurement only gives an average over a complete zone. While it is not a measurement that can be easily calibrated, the analogue response from this pulse excitation system will show small reflections predominantly from continuous water sections around the cable, by analysing this analogue reflection response additional information about the changing fluids can be obtained adding some subjective detail to the basic measurement. By detecting these details from sampling sections this will also allow the absence of these responses to indicate continuous or well mixed fluids.

Preferably the system comprises a plurality of elongate structures arranged within a fluid. In this way, the system provides a three-dimensional array (time, depth, and location) of measurement points within a fluid in which the system is immersed.

According to a second aspect of the present invention there is provided a method of determining fluid composition and flow rate in a conduit; the method comprising the steps:
 (a) locating a cable in the fluid through a length of the conduit, the cable comprising a plurality of physically separate sampling sections;
 (b) measuring an ambient temperature at a plurality of measurement points along the length of the conduit;
 (c) heating a core of the cable for a predetermined heating period, and taking temperature measurements at the same measurement points;
 (d) injecting a high frequency signal along the cable;
 (e) recording a response of an average velocity of propagation of the signal over each sampling section of the cable; and
 (f) determining distributed fluid type and a fluid velocity through the length of the conduit.

Preferably, a plurality of responses are recorded from reflections of the signal at interfaces between the sampling sections within the cable.

Preferably, the method includes the steps of identifying the ends of the sampling sections and identifying all non-fixed responses. More preferably, the method includes the step of using the presence of non-fixed responses to enhance interpretation of the response. The absence of a non-fixed response indicates a well mixed fluid whereas the non-fixed responses can be used to indicate the nature of the fluid flow across any sampling section and any discrete fluid changes in any sampling section.

Preferably, measurements for the determination of fluid mixture are used to adjust the velocity measurement to the correct fluid velocity measurement.

Preferably, pre-installed knowledge of appropriate fluid characteristics are used to obtain distributed fluid velocity measurements for the fluid passing over the surface of the cable.

Preferably, the method determines distributed and/or point fluid flow information from said distributed fluid velocity measurements in real-time.

Preferably, the method is further operable to use obtained or pre-installed knowledge of a number of fluid characteristics to identify which of said number of fluids it is immersed in at any one measurement point directly from the measured temperature at said particular measurement point after said predetermined heating period.

Preferably, the method includes the step of using probabilistic modelling to determine the distributed fluid velocity measurements. By this, for example, if a lower sampling section indicates continuous water then it can be determined that the lower end of the sampling section above it is probably continuous water too, so the interpretation of the next section is improved using this technique. This technique also embeds existing knowledge of reservoir fluid behaviour to some extent, with information such as gas is most likely to bubble upwards faster than the fluids, and not flow down slower than the fluids. These sorts of "knowledge" inputs improve the interpretation of the output from any given sampling section. So the probability of any given interpretation of the data being true is included in the processing of data, and used to indicate the most probable correct interpretation. This can also indicate a confidence factor on any output which in itself is also useful. In this way even in chaotic and complex fluid regimes, a most probable interpretation will always be arrived at. In addition in simple fluid regimes the probability of the interpretation being correct will be high, and in more complex it will be much lower, and this in itself is a measure of the nature of the fluid regime being measured, and as such is an output form this system.

Preferably, the conduit is a well bore or a pipeline where it can be used to detect and/or locate leaks and/or branches. The method may also comprise locating a plurality of cables in a fluid storage facility such as a tank, reservoir, separator etc.

Embodiments of the invention will now be described, by way of example only, by reference to the accompanying drawings, in which:

FIGS. 1 (*a*), (*b*) and (*c*) are cross-sectional and isometric views, respectively, of a cable for use in a fluid measurement system according to an embodiment of the present invention;

FIGS. 4 (*a*), (*b*) and (*c*) are schematic illustrations of a fluid measurement system being deployed in a well bore;

FIG. 7 is a schematic illustration of a fluid measurement system deployed in a body of fluid representative of a storage tank, separator, reservoir or the like;

FIG. 8 is a schematic illustration is an alternative arrangement of a fluid measurement system deployed in a body of moving fluid representative of a storage tank, separator, reservoir or the like;

FIG. 9 is a schematic illustration is further arrangement of a fluid measurement system deployed in a body of moving fluid representative of a storage tank, separator, reservoir or the like;

FIGS. 10 (*a*) and (*b*) are embodiments of a wire in a fluid measurement system;

Figures 1A, 1B:
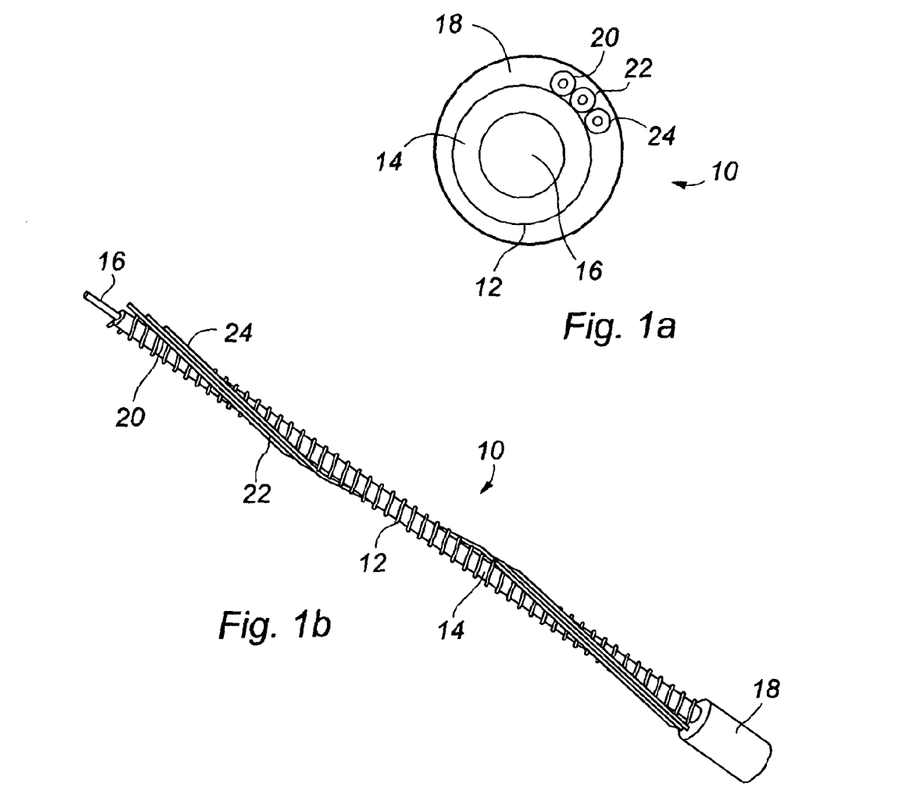
Figure 1C:
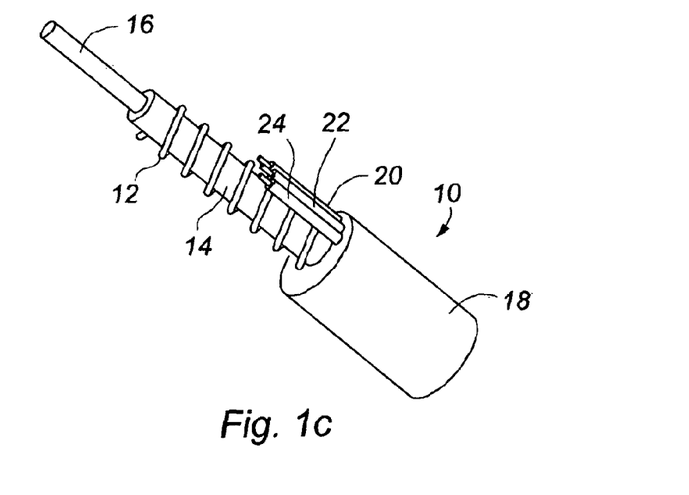

Reference is initially made to FIGS. 1(*a*),(*b*) and (*c*) of the drawings which illustrate an elongate structure being a cable, generally indicated by reference numeral 10, for use in a fluid measurement system according to embodiment of the present invention. Cable 10 comprises a helical wire core 12 wound on a high temperature liner 14 and a tensile heater core element 16. Around this is a high temperature resistant sheath 18. Spiraled around the outside of the main heater 16 and transmission line spiral core 12, and embedded within outer layer 18 is a fibre optic temperature sensor array 20, such as an ⅛ inch OD tube encapsulated fibre optic temperature probe, a ground return cable 22 and a data communication line 24. The cable is encapsulated by an outer shell 18. The data communication line 24 can be a cable, single, twisted pair or coax and also could be a further fibre optic line provided for high speed data transmission.

The heated core 16 can comprise any heat source means (including a heated fluid), but in a preferred embodiment comprises a current carrying wire heated by resistance heating. Using a resistance wire simplifies temperature control compared to other heating methods, and also provides for a uniform heat rise above ambient.

The fibre optic sensor array 20 may be any of the types known in the art The use of intrinsic fibre optic sensors to provide distributed temperature sensing over very large distances is well known. For example, temperature can be measured by using a fibre that has evanescent loss that varies with temperature, or by analysing the Raman scattering of the optical fibre.

The wire 12 is arranged helically along the insulating but thermally conducting liner 14. By providing a spiral cable assembly we can increase the separation between the leading and trailing edge responses of the high frequency pulse over equal lengths of cable. For example, a pulse edge travels typically at 200E6 m/s, so therefore the start and end responses from a 1 meter marker are only 5 nS apart (and the inverse of each other), in a long cable section of say 20 meters the responses are separated by 100 nS and so on. If we then also include a spiral cable assembly amplifying the effective length of the cable section by at least a factor of five we then have a 20 meter cable section with a 500 nS gap between leading and trailing edge responses. This technique can be extended by increasing the pitch of the spiral and also extending the length of the cable sections, until the system is operating at a practical bandwidth.

If a spiral sensor cable is used then the propagation length of the cable is increased by a large factor increasing the effective spatial resolution. As the system uses high frequency pulses, the time intervals being measured are extremely small making small spatial measurements very difficult. For a straight cable, very high speed pulse sources will be required to get good resolution especially in moving fluids where the changes in fluid mixture will both change quickly and also will change over relatively short physical distances. Thus the spiral cable will overcome this by increasing the effective spatial resolution.

The fluid measurement system using the cable 10 of FIG. 1 firstly operates by measuring the cooling effect resultant from the fluid or gas flowing over the surface of the cable 10. It does this, in one operational embodiment, by first measuring the ambient well bore temperature at each optical measurement point being considered, followed by switching the heated core on for a predetermined heating period, and then taking temperature measurements again at the same optical measurement points. The temperature rise caused by the heated core at each measurement point is dependent on the thermal cooling of the walls of the cable at that point, which in turn is dependent on, and therefore allows the measurement of, the fluid velocity characteristics around the cable surface at that point. The principle of fluid velocity measurement using cooling of a heated object is well proven and documented uses date back to 1904. The cable 10 secondly operates by passing a high frequency pulse down the wire 20 and measuring the response to provide an average velocity of propagation along the wire 20. This response is used to determine the fluid type or composition through which the cable 10 is immersed. In this embodiment, cable 10 is assumed to comprise a single sampling section for clarity.

Figure 2:
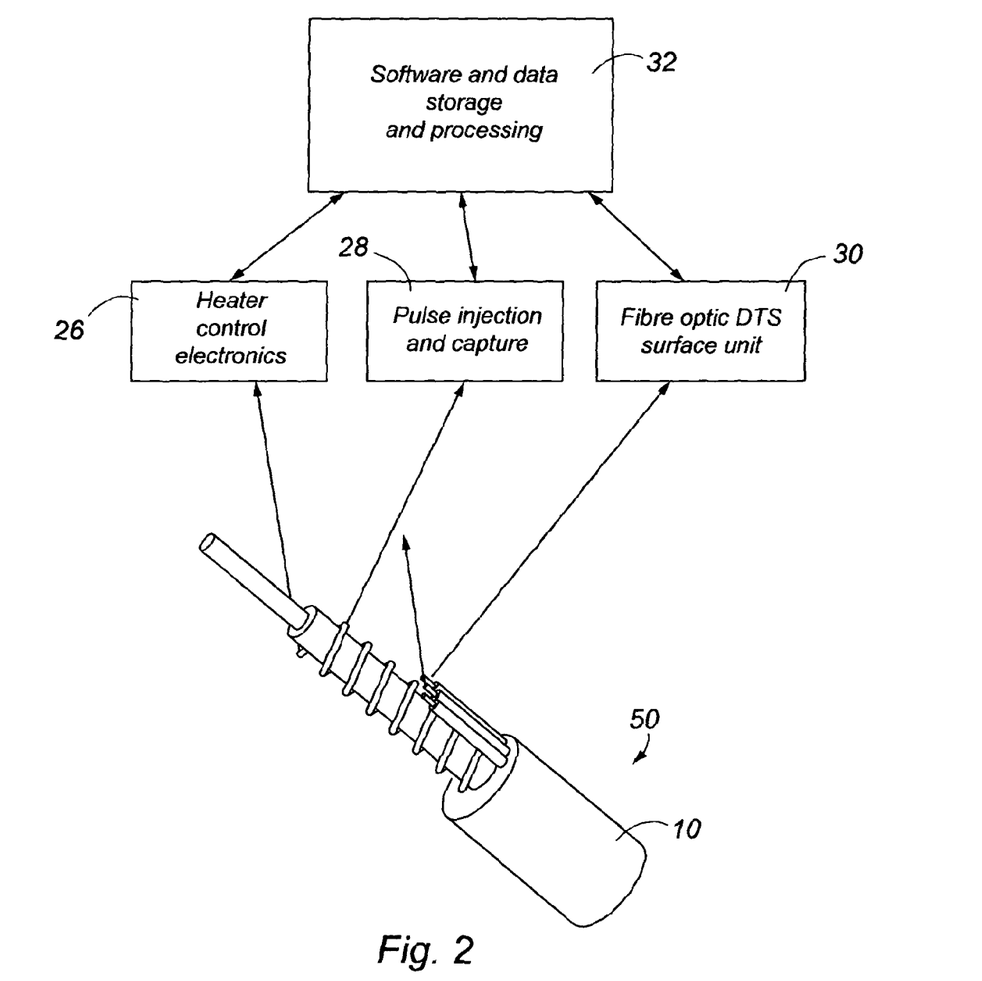
FIG. 2 is a schematic illustration of a fluid measurement system, using the cable of FIG. 1, according to an embodiment of the present invention.

FIG. 2 shows the main parts of a fluid measurement system, generally indicated by reference numeral 50, according to an embodiment of the present invention. The cable 10 connects functionally to the heater power and control unit 26, and also can be switched to attach to the pulse generator and data capture unit 28. The DTS fibre cable sensor 20 connects to the fibre optic processing unit 30 at surface, the ground return 22 is generally connected to the local ground connections, and the data connections 24 connect to the electronic modules allowing data transfer and control. A central data acquisition unit 32 connects each unit 26,28,30 to provide software, data storage and processing.

Figure 3:
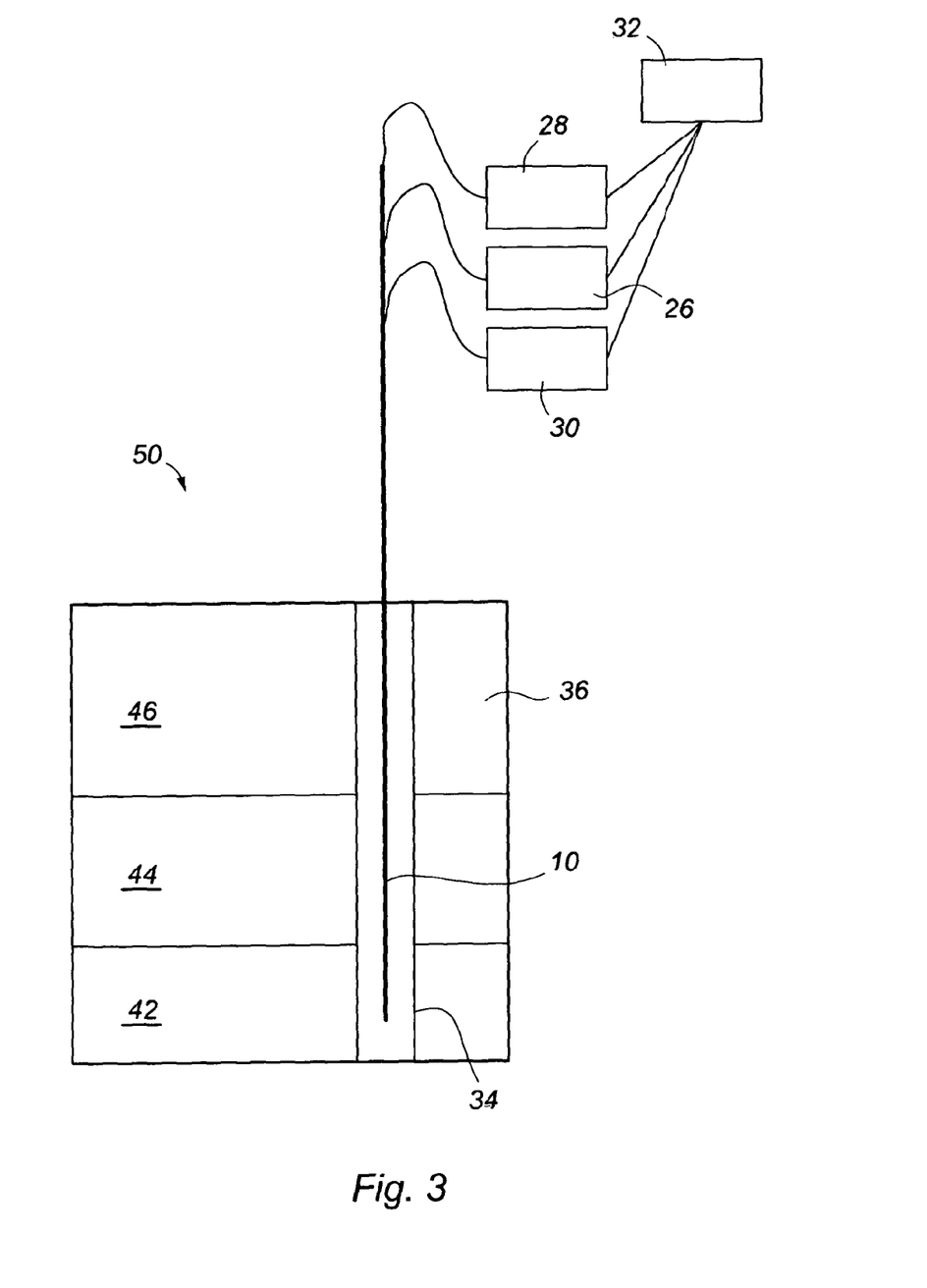
FIG. 3 is a schematic illustration of a fluid measurement system according to an embodiment of the present invention deployed in a wellbore.

FIG. 3 depicts a fluid measurement system 50 for use in oil and gas wells, or any deep well bore, or pipe line. The system 50 comprises a cable 10 which is deployed into the well bore 34 in reservoir 36 and a surface electronics control and processing unit 32,26,28,30, which controls the heaters, processes and records the information. The surface electronics control and processing unit shown here comprises a heater control 26, a fibre optic distributed temperature sensor (DTS) measurement apparatus 30, a pulse measurement unit 28 and a central data logger and data handling unit 32. The well bore 34 in this example contains a water layer 42, an oil layer 44 and a gas layer 46. The cable 10 can be many kilometres long, and be able to determine fluid type and distributed fluid flow rates along its full length.

In an embodiment, the data acquisition unit 32 compares the response to a probabilistic mathematical model of the well bore to determine the flow rate and/or mixture of fluids along the cable 10. By this, for example, if a lower sampling section indicates continuous water then it can be determined that the lower end of the sampling section above it is probably continuous water too, so the interpretation of the next section is improved using this technique. This technique also embeds existing knowledge of reservoir fluid behaviour to some extent, with information such as gas is most likely to bubble upwards faster than the fluids, and not flow down slower than the fluids. These sorts of "knowledge" inputs improve the interpretation of the output from any given sampling section. So the probability of any given interpretation of the data being true is included in the processing of data, and used to indicate the most probable correct interpretation. This can also indicate a confidence factor on any output which in itself is also useful. In this way even in chaotic and complex fluid regimes, a most probable interpretation will always be arrived at. In addition in simple fluid regimes the probability of the interpretation being correct will be high, and in more complex it will be much lower, and this in itself is a measure of the nature of the fluid regime being measured, and as such is an output from this system.

In a further embodiment, the system 50 includes an analogue detection unit, at 28. This allows the analogue reflection response to be analysed. In this way, while the average fluid mixture is measured, information about where the fluid mixture changes over a section can be obtained. The primary measurement only gives an average over a complete zone. While it is not a measurement that can be easily calibrated, the analogue response from this pulse excitation system will show small reflections predominantly from continuous water sections around the cable, by analysing this analogue reflection response additional information about the changing fluids can be obtained adding some subjective detail to the basic measurement.

Figure 4A:
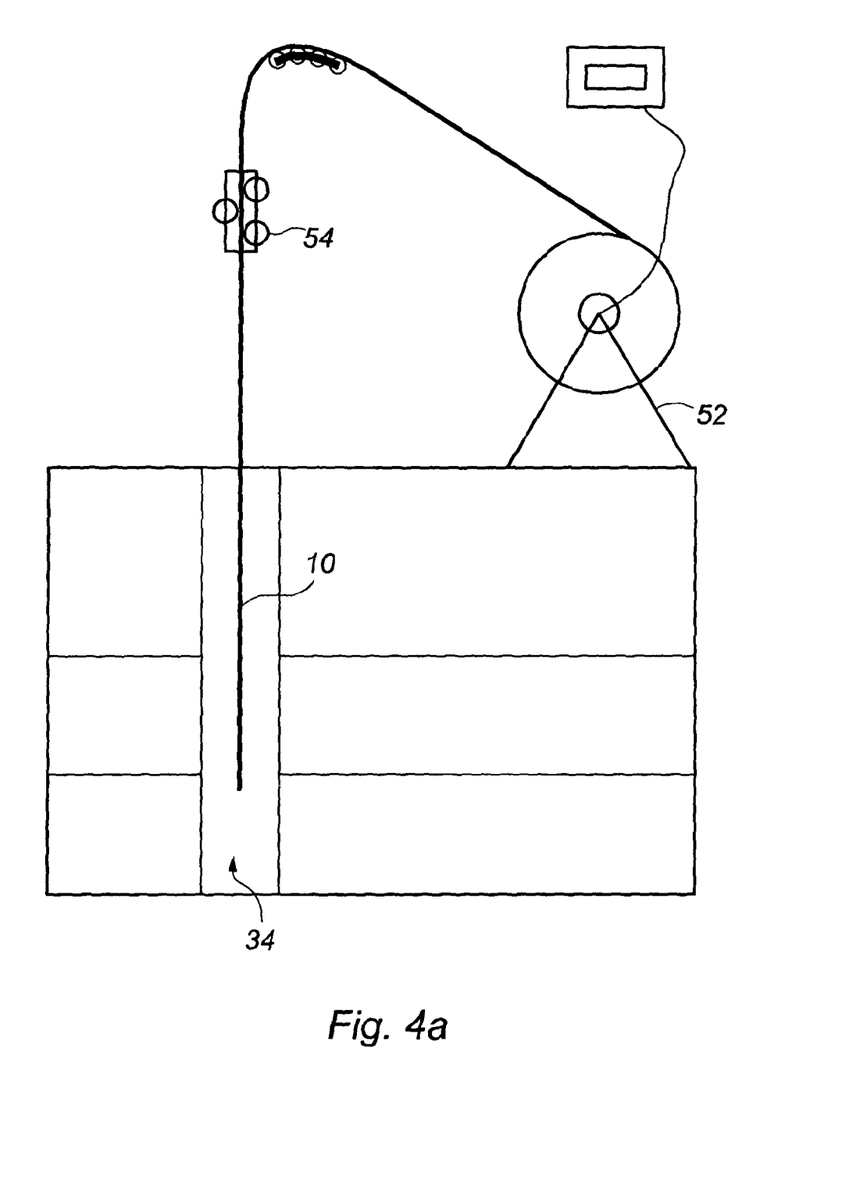
Figure 4B:
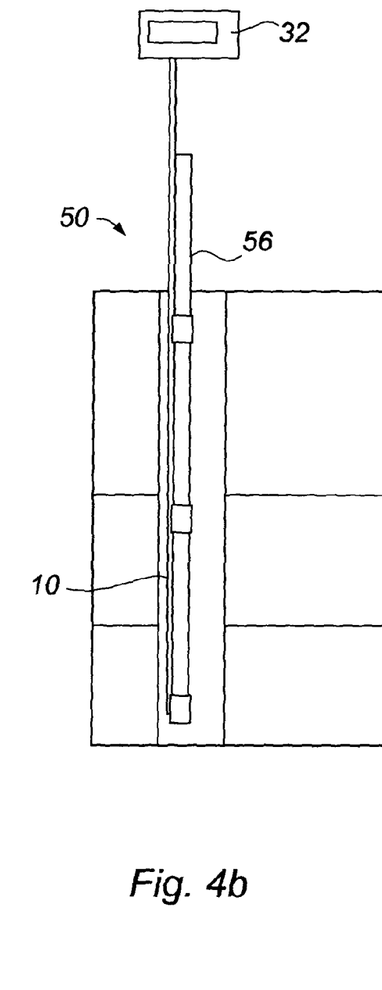
Figure 4C:
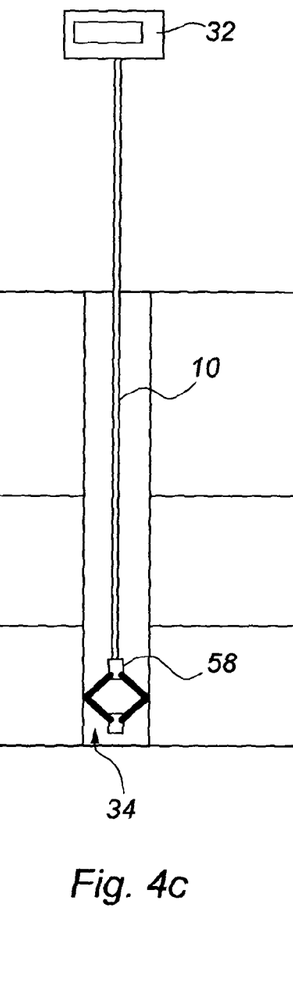

FIG. 4(a) illustrates the cable 10 being installed into a well bore 34 using a spooler unit 52 and an injector 54. In this embodiment, cable 10 is of a semi rigid construction to allow injection into the well bore 34, for example, the cable 10 may include a rigid element such as carbon fibre along its length. FIG. 4(b) shows an alternative deployment, wherein the system 50 including cable 10 and surface equipment 32 installed by strapping it to production oil field tubing 56. A further alternative deployment is shown in FIG. 4(c). The system 50 with cable 10 and surface equipment 32 is lowered into a well bore 34 suspended on weights from surface and held down hole with an anchor 58.

The cable based sensor array has many applications other than the measurement of fluid and gas flow characteristics over the length of an oil or gas well and the providing of information on the fluid being produced in each rock formation as already described.

Figure 5:
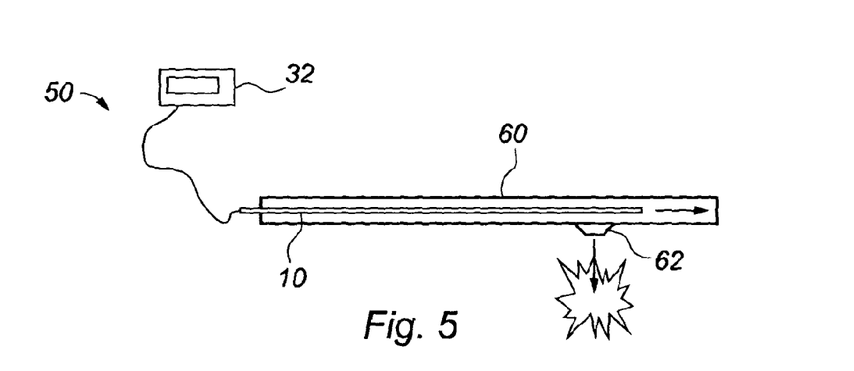
FIG. 5 is a schematic illustration of a fluid measurement system deployed in a pipeline containing a leak.

Reference is now made to FIG. 5 of the drawings which illustrates the system 50 used in a pipeline 60. Cable 10 is positioned along the pipeline 60 and fluid mixture composition and flow rates are determined along the length of the pipeline 60. The presence of a leak 62 will reduce the flow rate and change the composition detected at the position of the leak 62. In this way, the surface unit 62 can be programmed to alert the user when the conditions change indicative of a leak 62. As position is also determined the location of the leak 62 in the pipeline 60 is provided which can speed up the repair time.

Figure 6:
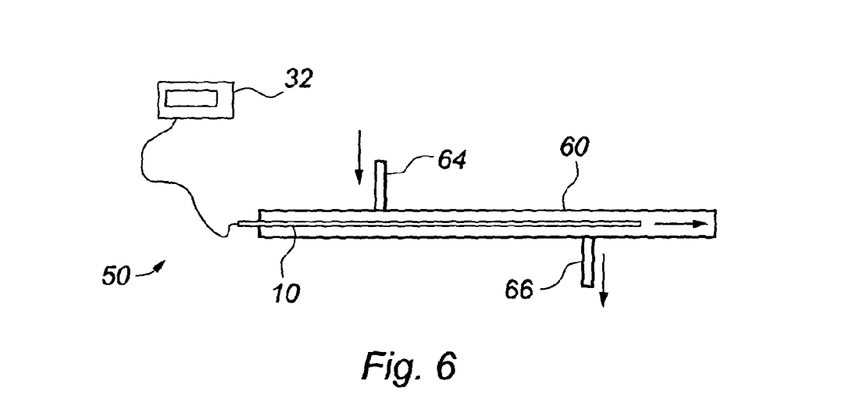
FIG. 6 is a schematic illustration of a fluid measurement system deployed in a pipeline having inlet and outlet branches.

While FIG. 5 showed an ability to detect failures in a pipeline, FIG. 6 illustrates the system 50 used to provide operational data on the position of injection points 64 or outlet branches 66. In each of these circumstances, fluid flow rates and composition in the main pipeline 60 is monitored, giving not only the location of the injected fluid 64 and drained fluid 66, but also the effect of these connections on the flow rate and composition in the main pipeline 60. It will be apparent that any number of inlets and outlets can be monitored along the pipeline 60. Additionally, in smaller forms, the system 50 could be deployed across the diameter of a pipe to measure in real time the flow profile in a pipe.

Figure 7:
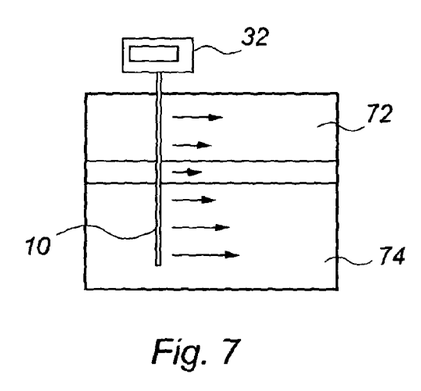
Figure 8:
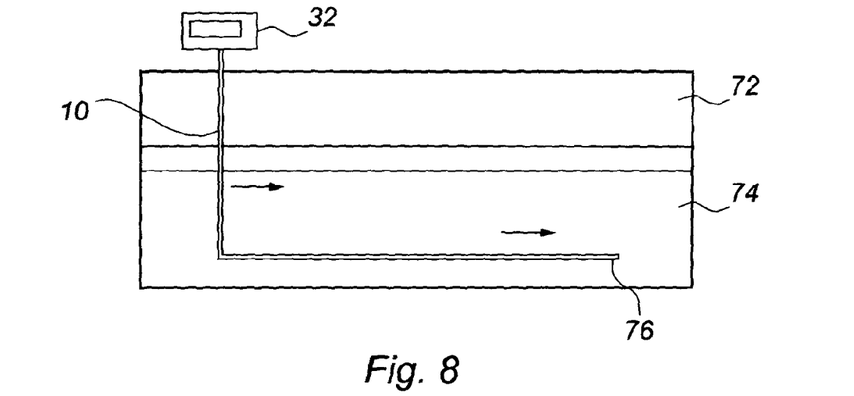
Figure 9:
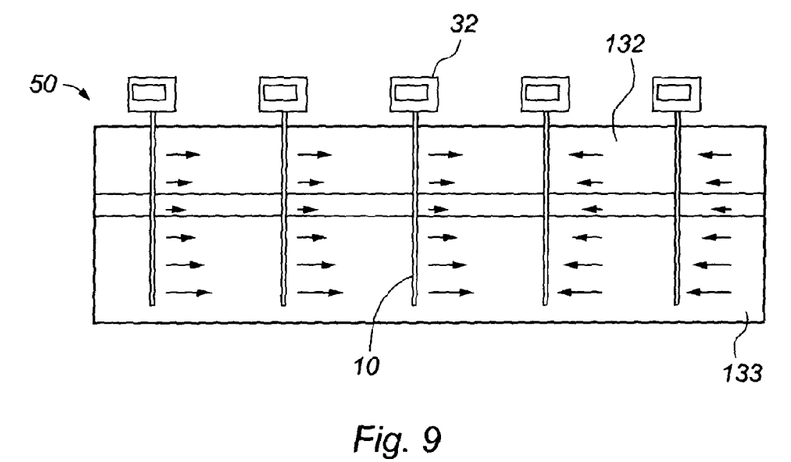

Reference is now made to FIGS. 7, 8 and 9 which illustrate further operational embodiments where the fluid measurement system 50 is deployed in a storage tank, separator or even reservoir, such as a ground cavern, or any other large body of fluid, generally indicated by reference numeral 70. In the first example, FIG. 7, only one cable 10 is being used. Here the cable 10 is arranged vertically through the body of fluid 70 but it could take any configuration, whether L-shaped (as illustrated in FIG. 8), or vertical, horizontal or any other two- or three-dimensional configuration. In FIG. 7, the vertical position will provide a depth position for the fluid 72,74 change points together with cross flow rates across the body 70 at a single location. Use of a horizontally arranged section of cable 76 as illustrated in FIG. 8, provides the same information but also gives flow rate through the body 70 for a single fluid 74, which would be useful if the body 70 is a separator and the heaviest fluid 70 is being drained off.

The second example, shown in FIG. 9, depicts a plurality of systems 50 (one row of cable arrays 10 is shown, but there may be more) which can be used to create a three-dimensional model of the flowing behaviour of the complete reservoir or tank. Again, each cable 10 could take another configuration. Also, while each cable 10 is shown with a dedicated control and processing unit 32, the system may instead have a single control and processing unit for all the cables 10, or a subset thereof.

Figure 10A:
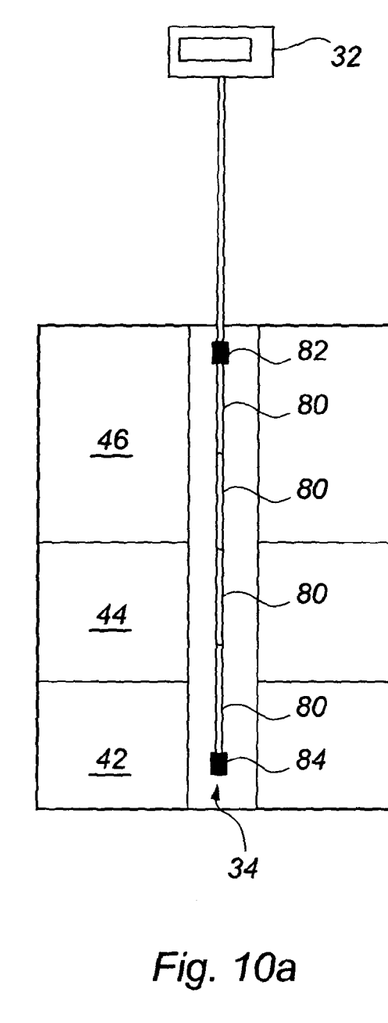

In the present invention, the fluid composition measurement is improved by forming the wire 12 into portions 80 or sampling sections. We seek to provide an impedance barrier between the portions 80, which can be achieved by forming the wire 12 as alternating portions of wire with differing characteristic impedance. This is illustrated in FIG. 10(a). The interface between the changing portions 80 will provide a response which can be used as a reference for the velocity in each portion 80. In FIG. 10(a), the system 50 includes two electronic modules top 82 and bottom 84 of the wire 12, a single wire 12 made up of alternating portions 80 of differing construction, all connected to a surface system 32. The data acquisition unit 32 may interpret the response for a portion 80 by using the average properties in the adjacent portions of the well bore as described hereinbefore in relation to the probabilistic modelling. Additionally, the data acquisition unit 32 may provide interpretation by looking at incremental changes between portions 80. In this way, while a two phase fluid mixture such as oil and gas or water and gas or water and oil, is easily determined, interpretation and use of a model will aid determination where there are three phases of fluids present, water oil and gas simultaneously.

Figure 10B:
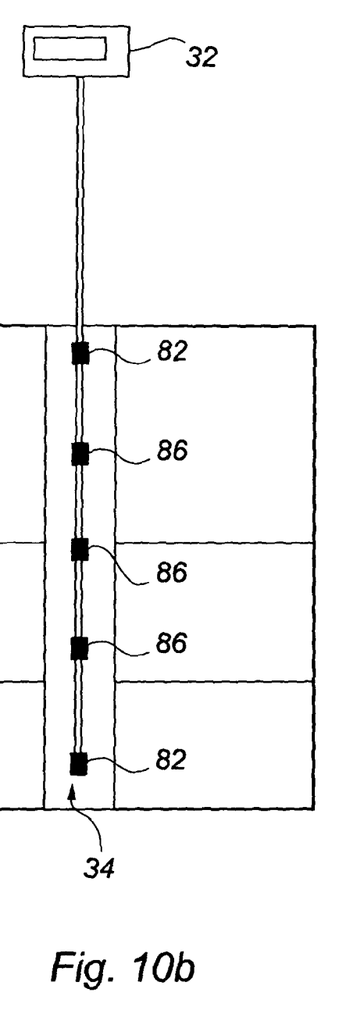

An alternative arrangement is illustrated in FIG. 10(b). Wire 12 is now made up of several shorter lengths of wire 80 with electronic modules 86 between each sampling section 80. It again has an upper electronic module 82 and lower module 84, and a surface system 32. The wellbore 34 contains water 42 oil 44 and gas 46 but in any order and not necessarily in a simple vertical layer as shown. By taking measurements at both ends of the wire 12 or portions 80, the system 50 may be effective in deep well bores to operate over long propagation sections by limiting the effects from losses in the wire 12 and also from progressively more confusing responses from the further away portions 80 of the wire.

In use, the system 50 as described in FIG. 10(*a*) or 10(*b*) is deployed as described herein with reference to FIGS. 4 to 9. The distributed temperature sensor 20 operates by recording the cooling effect at the surface of the cable 10, following heating by the heat element 16. At the same time the signal generator injects a high frequency signal (rise time, typically <5 nS) through the wire 12 and its response is detected at the surface 32 via the module 28. The signal may be modulated carriers, pulse streams, pulse sequences and shorter simpler pulse bursts. Advantageously, a PN sequence of high frequency pulses is used to remove the major problem of extracting valid reflections from other responses and noise from the system 50 when a simple pulse reflection is used for the measurement of pulse velocities. If a PN sequence of high frequency pulses is transmitted instead of a single pulse and the response from the system is then compared looking for the correct pulse sequence, the resolution and potential cable depth which can be measured increases. Where PN sequence signal sources are used these can run both real time and continuously in parallel. Advantageously, orthogonal PN sequences may be used so that two or more pulse sequences do not interfere with one another.

By a combination of the distributed temperature sensor 20 and the high frequency pulse response on the air 12, the system 50 can be used to measure the cable surface cooling and determine the fluid characteristics at all points along each sampling section 80 of the cable 10 length, and therefore determine the fluid velocity at any point along the cable 10. From this sensor surface velocity information the processing unit 32 can calculate fluid flow rates in real time. This is achieved through probabilistic modelling.

In one embodiment, the method is carried out by immersing the cable 10 in one or more fluids over its whole length; injecting one or more high frequency pulses into the transmission line wires in the cable and recording the response from the wire to these injected pulses; establishing the average pulse velocity in each separate measurement portion of the wire, by directly measuring the time of travel; measuring the ambient temperature of the fluids at a plurality of measurement points along the length; turning on the heated core for a predetermined heating period; measuring the temperature again at the same measurement points; calculating the difference between the normal and heated conditions, the difference being proportional to fluid velocity for any given fluid or gas.

When several portions 80 with discrete electronics 86 are used the velocity is obtained from direct measurement. Where a segmented wire 12 is used, time of travel of the portion 80 nearest the surface system 32 is established first. This is then subtracted from the transit time from the second portion and so on until a separate measurement is recovered for each portion 80. These velocities are then compared to the calibrated velocities for this type of cable and the fluid mixture is determined.

Obtained or pre-installed knowledge of the appropriate fluid characteristics can be used to process the distributed cooling measurements to obtain distributed and/or point fluid velocity measurements for the fluid or fluids passing over the surface of the cable. Real-time distributed and/or point fluid flow information can be determined from the distributed and/or point fluid velocity measurements.

Further embodiments include obtaining information to identify the fluid or fluids at the same time as performing the distributed cooling measurements; and using obtained or pre-installed knowledge of a number of fluid characteristics to identify which of the number of fluids it is immersed in at any one measurement point directly from the measured temperature at the measurement point after predetermined heating.

It is an inherent problem of this type of measurement that false reflections can be obtained from mechanical damage in the cable and also severe changes in the surrounding fluids. A further technique to remove these false reflections is to have the lower electronics module in any sensing portion change the lower termination impedance. This then creates a definitive system reflection which can be separated from any false responses as it changes under system control.

A further technique to assist with discrimination of false responses is to generate a mathematical model of the transmission line and compare the output of this model with the actual response. This will indicate where the cable end and cable portion responses should be, and can assist with removal of false reflections. Note that these false reflections if created by fluid changes are the very image information which can give an indication of where the fluid is changing in nature. So by inference these two techniques for identification of the correct reflection responses will also by definition allow responses from the fluid changing to be isolated and analysed.

Figure 11:
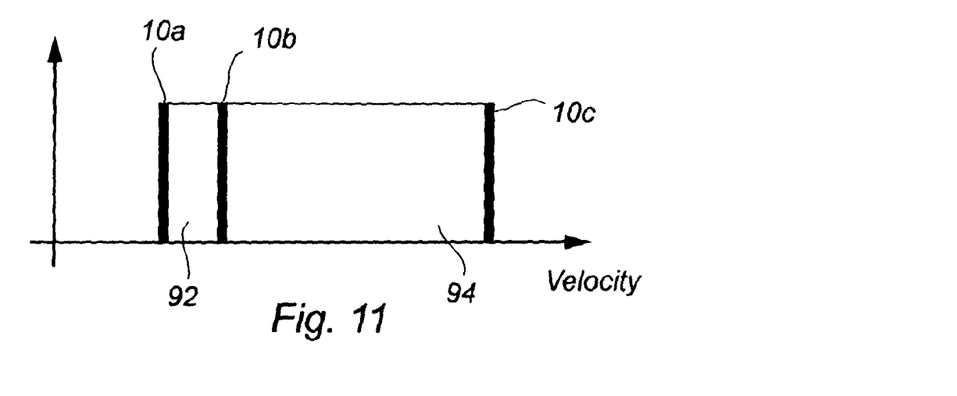
FIGS. 11, 12 and 13 show typical calibration data for the measurements.

FIG. 11 shows the calibration outline of the pulse velocity measurement. This is showing the velocity of the pulse 90 with air or gas surrounding the cable 10*a* and with oil surrounding the cable 10*b* and with salt water surrounding the cable 10*c*. It can be seen that if the pulse velocity lies in the first zone 92 it is a mixture of oil and gas and in the second zone 94 it is a mixture of salt water and either oil and gas or one of the two.

Figure 12:
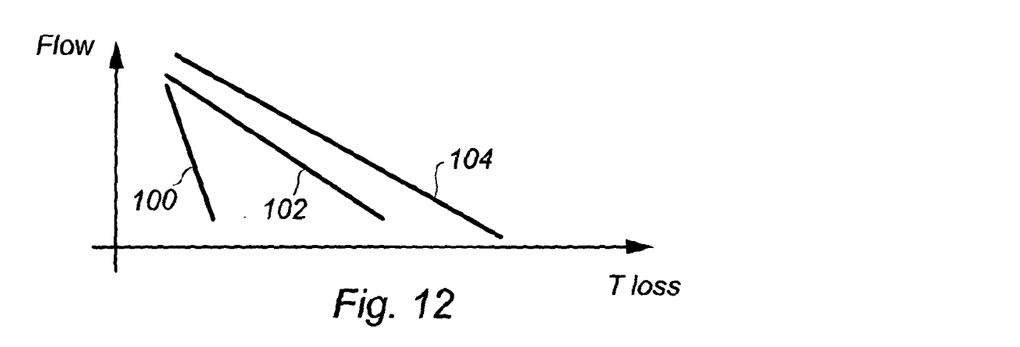

FIG. 12 shows the temperature difference output from thermal cooling on the distributed temperature sensor 20. Temperature loss is shown against flow 98, showing the differing responses in air or gas 100, in oil 102 and salt water 104. This clearly shows that these calibrations overlap and to be able to work out velocity the fluid type must be known.

Figure 13:
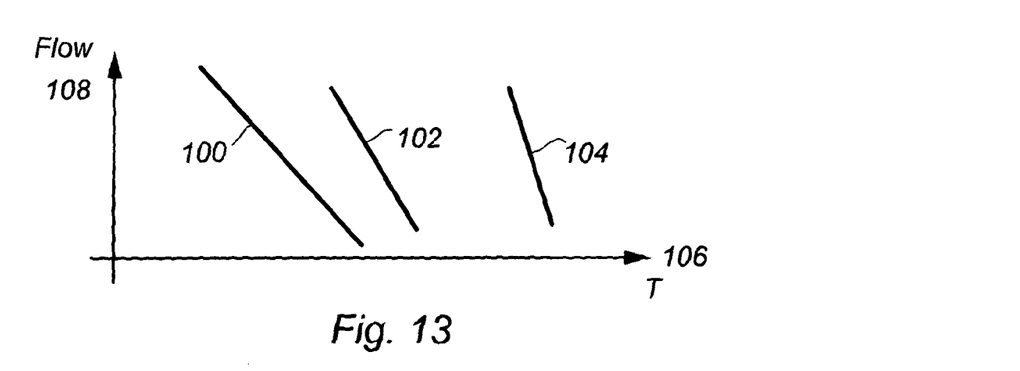

FIG. 13 shows the range of absolute temperatures 106 measured against flow 108 with the heater 16 powered. Three straight line plots are shown for the different fluids with air or gas 100, oil 102 and water 104. This clearly shows that with high volumetric amounts of gas the fact that the measurement reaches much higher temperatures is in itself an indication of the presence of gas. Any absolute measured temperature above the highest point in calibration curve 102 must have a percentage of gas present. This example implies and implicitly requires the sensor construction to include the temperature sensor and heater in a thermally isolated construction to ensure and control the thermal characteristics to ensure this beneficial behaviour is true, and optimised for this purpose. This behaviour is difficult to control with a high powered or highly exposed heater.

It will be apparent that the graphs presented in FIGS. 11,12 and 13 are simplified for the purpose of illustration and these responses may need to be linearised and compensated for temperature shift to get to the linear responses shown. The sensor construction also has to allow for the thermal coupling from the heater to the fluid to be optimised which can only be done in a structure with a outer casing which can be of a particular material and/or a controlled thickness and in this way a predictable and favourable response can be obtained.

Figure 14:
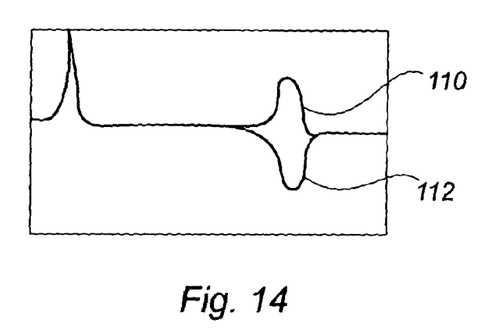
FIG. 14 illustrates the effect of altering the cable termination impedance.

FIG. 14 illustrates the effect of placing a low 110 or high 112 impedance termination on the end of the transmission line cable. This technique can provide absolute measures of where in the time space of the trace the end of the cable 10 is since the change in the reflective waveform can be securely attributed to the change in termination impedance and not any other activity in the sensing system 50, such as fluid changes.

Figure 15:
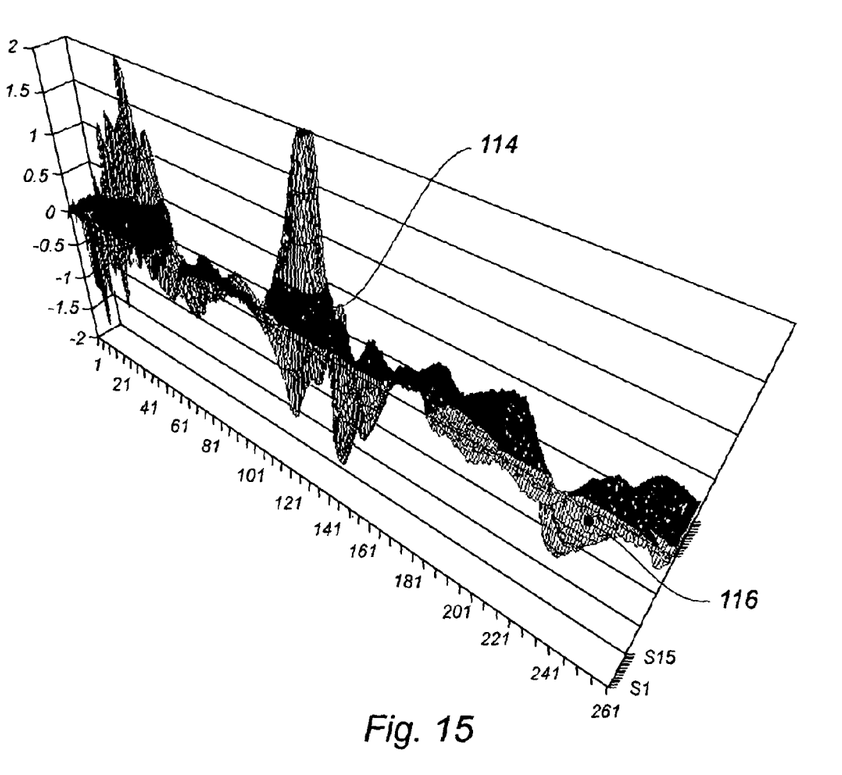
FIG. 15 shows the result of imaging the analogue pulse response.

FIG. 15 shows reflections from a single ten meter cable 10 sensing section with the fluid mixture changing with time, showing that the location along the ten meter section where the changes are most pronounced can be seen in this type of image. The most dramatic change is in the first area 114 half way down the section and a less dramatic but noticeable at the second area 116, near one end.

The principle advantage of the present invention is that it can accurately determine fluid flow rates in identified fluid mixtures. This can be achieved in two or three dimensions by the immersion of one or more cables into the fluid.

While specific embodiments of the invention have been described above, it will be appreciated that the invention may be practiced otherwise than as described. For example, features of the invention, such as those for processing, may take the form of a computer program containing one or more sequences of machine-readable instructions describing a method as disclosed above, or a data storage medium (e.g. semiconductor memory, magnetic or optical disk) having such a computer program stored therein.

The invention claimed is:

1. A fluid measurement system for measuring moving fluid along a length of a conduit comprising:
    an elongate structure physically divided into a plurality of sampling sections along it's length and located in the conduit;
    a heated core element and a distributed temperature sensor along the length of the structure, said heated core element and said distributed temperature sensor arranged so that the temperature sensor is physically between the heated core and an outside surface of the structure to sense heat loss from the core to its environment, and said heated core element and said distributed temperature sensor are encased in a material which thermally isolates the heated core element from the moving fluid;
    one or more wires arranged along the length of the structure, said wires being configured to be usable as a transmission line;
    at least one high frequency pulse generator for injecting a high frequency pulse along at least one sampling section of the structure; and a data acquisition unit for recording the heat loss along the distributed temperature sensor and the velocity of the high frequency pulse along each sampling section of the structure to provide a two-dimensional measure of fluid type and velocity simultaneously for the length of the conduit.

2. A fluid measurement system according to claim 1 wherein the elongate structure is a cable.

3. A fluid measurement system according to claim 1 wherein the distributed temperature sensor comprises a fibre-optic distributed temperature sensor.

4. A fluid measurement system according to claim 1 wherein the heated core element comprises a resistance wire.

5. A fluid measurement system according to claim 1 wherein the distributed temperature sensor, heater core and any wire used as a transmission line is coiled helically to change the spatial resolution.

6. A fluid measurement system according to claim 1 wherein the elongate structure includes an insulation layer enclosing the heated core element and the distributed temperature sensor is embedded within the insulation layer.

7. A fluid measurement system according to claim 1 wherein the elongate structure includes an insulation layer enclosing the heated core element and there is a second layer around the insulation layer and the distributed temperature sensor is embedded in the second layer.

8. A fluid measurement system according to claim 1 wherein the high frequency signal generator provides a signal with a fast rise time.

9. A fluid measurement system according to claim 1 wherein the signal is selected from a group comprising: modulated carriers, pulse streams, pulse sequences and shorter simpler pulse bursts.

10. A fluid measurement system according to claim 1 wherein the wire has a plurality of propagation sections, being the sampling sections, with neighbouring propagation sections having different characteristic impedances.

11. A fluid measurement system according to claim 10 wherein the data acquisition unit compares the measured heat loss and the velocity of the high frequency signal response to a mathematical model to determine the mixture of fluids in each propagation section.

12. A fluid measurement system according to claim 10 wherein the data acquisition unit interprets the response for a section by using the average properties in adjacent sections.

13. A fluid measurement system according to claim 10 wherein the data acquisition unit provides interpretation by looking at incremental changes between sections.

14. A fluid measurement system according to claim 10 wherein measurement electronics are mounted at each end of each sampling section.

15. A fluid measurement system according to claim 1 wherein the wire is arranged helically along the elongate structure.

16. A fluid measurement system according to claim 1 wherein the system includes an analogue detection unit and means to analyse an analogue reflection response.

17. A fluid measurement system according to claim 1 wherein the system comprises a plurality of elongate structures arranged within a fluid.

18. A method of determining fluid composition and flow rate in a conduit; the method comprising the steps:
    (a) locating a cable in the fluid through a length of the conduit, the cable comprising a plurality of physically separate sampling sections;
    (b) measuring an ambient temperature at a plurality of measurement points along the length of the conduit;
    (c) heating a core of the cable for a predetermined heating period, and taking temperature measurements at the same measurement points;
    (d) injecting a high frequency signal along the cable;
    (e) recording a response of an average velocity of propagation of the signal over each sampling section of the cable; and
    (f) determining distributed fluid type and a fluid velocity through the length of the conduit.

19. A method of determining fluid composition and flow rate in a conduit according to claim 18 wherein a plurality of responses are recorded from reflections of the signal at interfaces between the sampling sections within the cable.

20. A method of determining fluid composition and flow rate in a conduit according to claim 18 wherein the method includes the steps of identifying the ends of the sampling sections and identifying all non-fixed responses.

* * * * *